United States Patent [19]

Nagamune et al.

[11] Patent Number: 4,561,779
[45] Date of Patent: Dec. 31, 1985

[54] INSTRUMENT FOR MEASURING CONCENTRATION OF SUBSTANCE IN SUSPENSION

[75] Inventors: Teruyuki Nagamune, Wako; Ichiro Inoue, Tokyo; Noburu Takematsu, Kawagoe, all of Japan

[73] Assignee: Rikagaku Kenkyusho, Wako, Japan

[21] Appl. No.: 456,414

[22] Filed: Jan. 7, 1983

[51] Int. Cl.$^4$ ............................................. G01N 21/01
[52] U.S. Cl. .................................. 356/442; 250/573; 356/440
[58] Field of Search ............... 356/440, 441, 442, 436, 356/432, 435, 319, 323, 324, 325; 250/573, 574, 576, 564–565

[56] References Cited

U.S. PATENT DOCUMENTS

| | | | |
|---|---|---|---|
| 2,580,500 | 1/1952 | Albert | 250/574 X |
| 3,141,094 | 7/1964 | Strickler | 356/440 X |
| 3,516,746 | 6/1970 | Shibata et al. | 356/319 |
| 3,734,629 | 5/1973 | Griffiths et al. | 250/573 |
| 3,819,278 | 6/1974 | Muller | 356/442 |
| 3,994,585 | 11/1976 | Frey | 356/414 |
| 4,075,062 | 2/1978 | Shibata et al. | 356/442 |
| 4,193,694 | 3/1980 | Smith | 356/411 |
| 4,310,249 | 1/1982 | Kramer | 356/236 |

OTHER PUBLICATIONS

Y. H. Lee, "Pulsed Light Probe for Cell Density Measurement", *Biotechnology and Bioengineering*, vol. XXIII, pp. 1903–1906, 1981.

*Primary Examiner*—Vincent P. McGraw
*Assistant Examiner*—Robert D. V. Thompson, III
*Attorney, Agent, or Firm*—Brumbaugh, Graves, Donohue & Raymond

[57] ABSTRACT

Disclosed is an improved turbidimeter or instrument for measuring the concentration of a suspension using diffuser means for converting incident light into diffused light before passing through a suspension. The use of diffused light improves the linearity of the optical density vs. concentration characteristics over a relatively wide range.

5 Claims, 12 Drawing Figures

INSTRUMENT FOR MEASURING CONCENTRATION OF SUBSTANCE IN SUSPENSION

BACKGROUND AND SUMMARY OF INVENTION

The present invention relates to an improvement in or relating to an instrument for determining the amount of particles in suspension contained per unit of volume, and more specifically to an instrument for determining the concentration of a suspension in terms of absorption of light by particles in suspension.

BRIEF DESCRIPTION OF THE DRAWINGS

Turbidimeters and colorimeters are well known as such optical instruments. FIG. 1A shows a turbidimeter as a dual optical channel arrangement consisted of a reference channel and a test channel, each including a cell $1t$ or $1r$, a pin-holed shield $2t$ or $2r$ and a photodetector $3t$ or $3r$ in the order named. In operation, a medium containing particles in suspension or a suspension is filled in the test cell $1t$, whereas a medium containing no particles is filled in the reference cell $1r$. Collimated light is projected both to the test cell $1t$ and the reference cell $1r$. Each pin-holed shelter allows a single ray of transmitted light to fall on an associated photodetector $3t$ or $3r$. Specifically, in the reference channel a single ray is selected to pass through the shield $2r$, and the remaining rays of collimated light are rejected. Likewise, in the test channel after collision and absorption by particles a single ray is selected to pass through the shield $2t$, and the remaining rays of collimated and scattered light are rejected. Thus, the intensity of transmitted ray through the suspension is compared with that of transmitted ray through the medium to determine the optical density of the suspension which represents the concentration of the suspension. The concentration of the suspension is determined from optical density vs. concentration characteristics experimentally determined for the medium used. This turbidimeter shows a good linearity with a relatively high sensitivity within a relatively low range of concentration but it shows non-linearity at an increased concentration (See dot-and-dash curve in FIG. 4). This non-linearity is attributable to the selective use of a single ray with the aid of a pinhole. The single ray of light is easy to fade as the concentration increases above a certain threshold.

FIG. 1B shows a colorimeter as a similar dual optical channel arrangement. This instrument is sensitive both to collimated and diffused components of the transmitted light. This device shows non-linearity within a relatively low concentration range, but it shows a good linearity over a relatively high concentration range (See broken line curve in FIG. 4). FIGS. 2A–2C show how collimated and diffused components of the transmitted light vary in amount with the increase of particles in suspension. Specifically, as shown in FIG. 2A, collimated component is predominant in the transmitted light at a reduced concentration. As seen in FIGS. 2B and 2C, diffused component is increasingly predominant with the increase of particles in suspension until collimated component has disappeard in the transmitted light. The linearity of optical density vs. concentration characteristics appears when the collimated component disappears in the transmitted light, and then the photodetector $3t$ receives the diffused light only. It should be noted that the average distance that collimated component can travel before completely absorbed by particles in suspension is reduced with the increase of concentration as seen FIGS. 2A–2C. The non-linearity of the colorimeter in a relatively low concentration range is attributable to the fact that the instrument is sensitive both to collimated and diffused components in the transmitted light, each having obtained a piece of information of concentration in different ways and being modified differently in strength. Specifically, a part of the incident collimated light impinges an particles on the way to the photodetector, passing through particles and losing a part of energy by absorption. On the other hand, another part of the incident collimated light impinges particles instead of passing therethrough it is scattered and converted into diffused light, losing a part of energy by absorption at the time of collision.

In view of the above an object of this invention is to provide an instrument for determining the concentration of a solution in terms of optical density, assuring the linearity of measurement over its full range.

Another object is to provide an optical densitometer which facilitates automatic monitoring of fermentation process, such as cultivation of bacteria, yeast, mycelia or fungi, and hence full automization of fermentation.

To attain these objects an optical densitometer according to this invention uses a light diffusing means for converting incident light to diffused light before passing through a suspension. According to another aspect of this invention a optical densitometer uses another light diffusing means for the purpose of collecting the transmitted light prior to detection.

This invention will be better understood from the following description of preferred embodiments shown in FIGS. 3–8.

Figure 1:
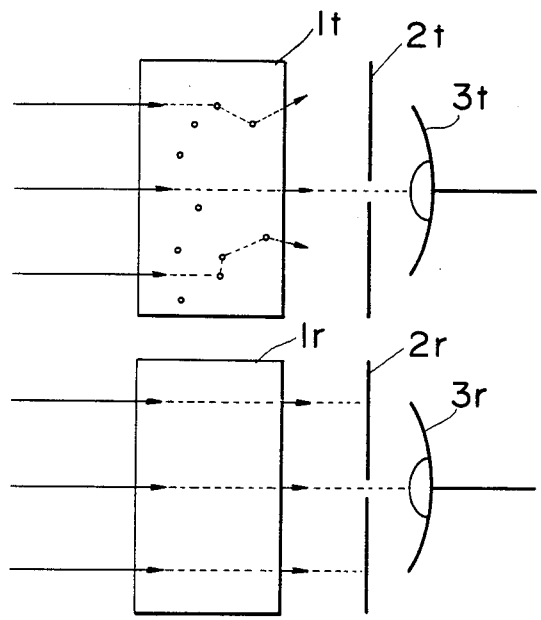
FIGS. 1A–1B show a turbimeter as a dual optical channel arrangement.
Figure 1:
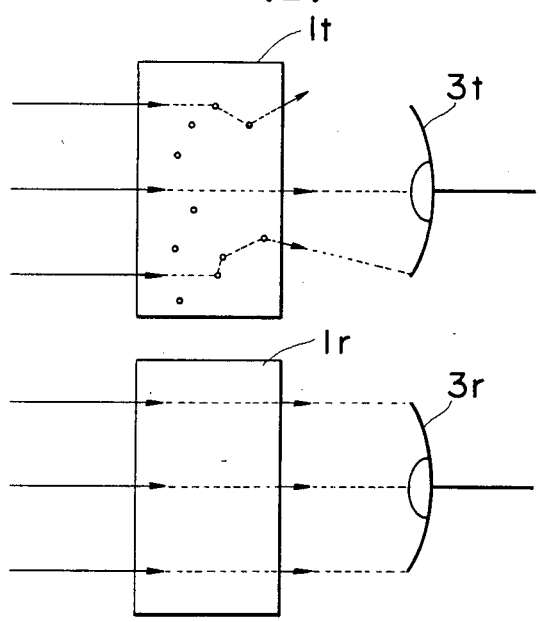
Figure 2:
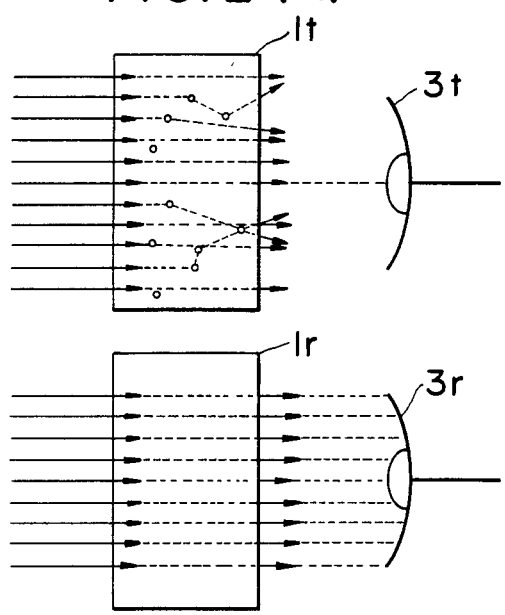
FIGS. 2A–2C show how collimated and diffused components of transmitted light vary with an increase in particle suspension.
Figure 2:
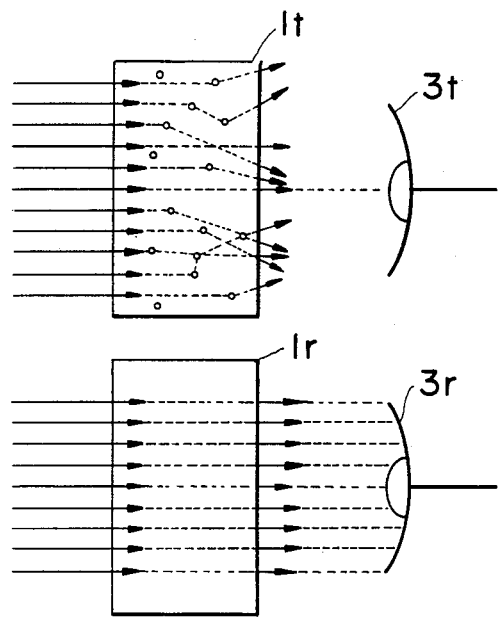
Figure 2:
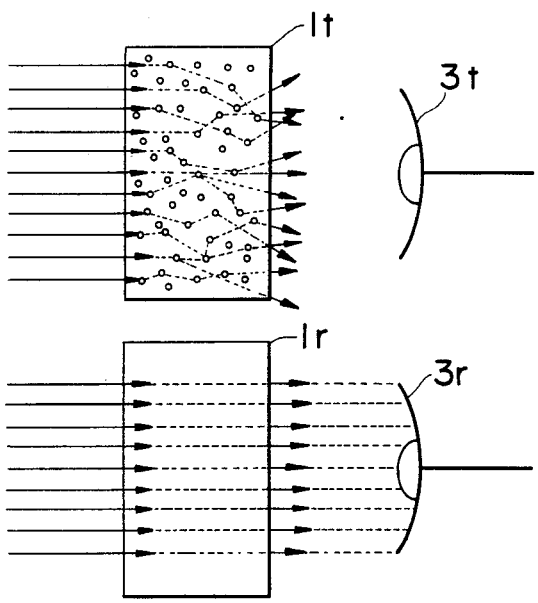
Figure 3:
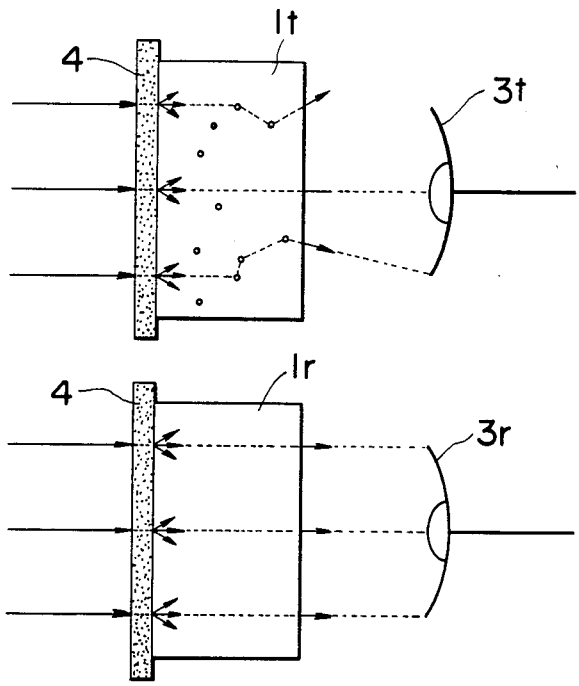
FIGS. 3A–3B show different dual optical arrangements of the invention.
Figure 3:
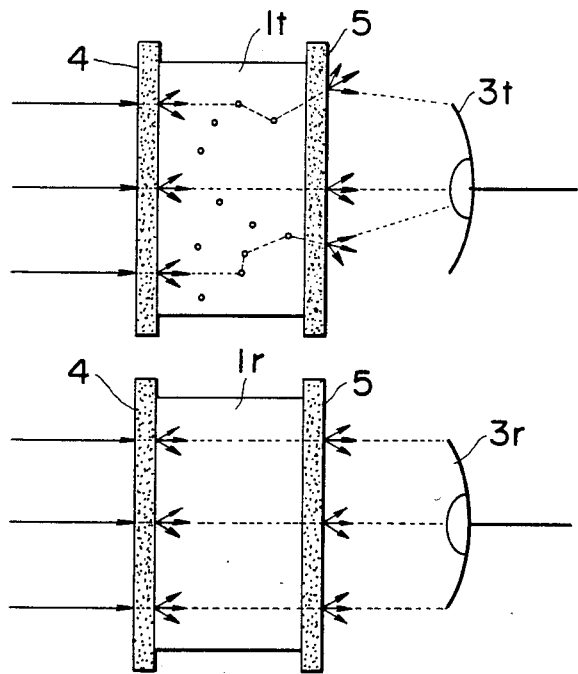

FIG. 3A shows a first embodiment of this invention as a dual optical arrangement, each including a transparent cell $1t$ or $1r$, a light diffusing plate 4 put on one side of the cell and a detector $3t$ or $3r$ in the vicinity of the other side of the cell. In operation, collimated light or divergent light falls on the diffuser plate 4 in each of test and reference channels. The incident light after passing through the diffuser plate is converted to diffused light. Thus, all the particles in suspension are exposed to the flood of diffused light (FIG. 3A). This situation is akin to that in which a colorimeter detects the concentration of a solution above a certain threshold above which the optical density vs. concentration characteristics show a good linearity (See FIGS. 2B and 2C, and FIG. 4).

Figure 4:
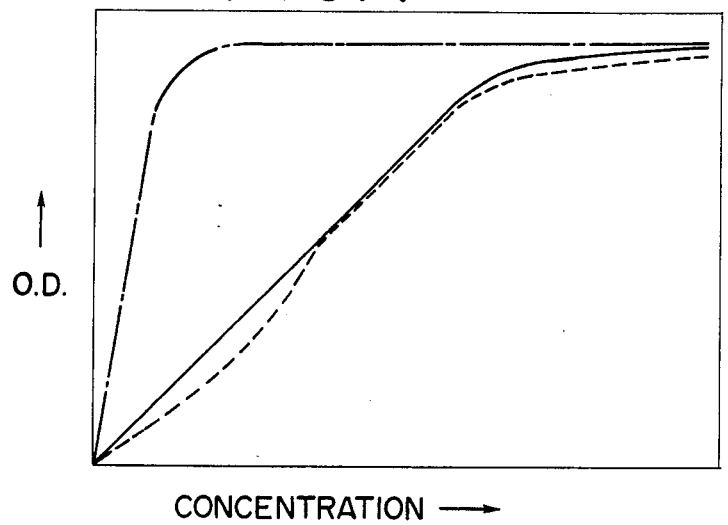
FIG. 4 shows a plot of optical density versus concentration.
Figure 8:
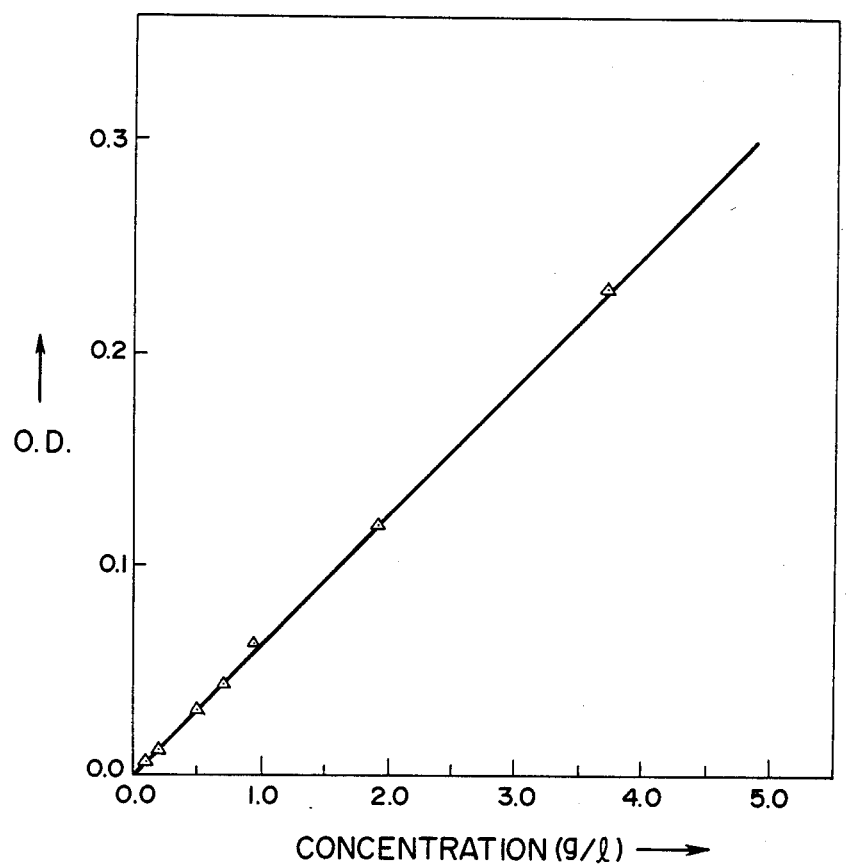
FIG. 8 shows a plot of optical density versus concentration.

Thanks to the use of diffused light an optical densitometer according to this invention has a good linearity over its full range as shown in FIG. 4 (solid line). In order to improve the sensitivity of the instrument it is necessary to determine the distance from the cell to the detector in consideration of the light-falling area of the detector and the light-emitting area of the cell lest a substantial part of transmitted light should miss the target area of the detector 3t.

FIG. 3B shows a second embodiment as including a cell two diffuser plates sandwiching the cell and a photodetector in each channel. The second diffuser plate 5 is used for the purpose of converting every ray of transmitted light into diffused light having different components in all direction. At least one component of the converted light is directed to the target area of the photodetector. Thus a proportional amount of transmitted rays are picked up and directed to the photodetector. As is understood from the above, the second diffuser permits the use of a relatively small target area for a relatively large cell. Also, it should be noted that a cell is thin enough to assure that every scattered ray falls on the second diffuser. FIGS. 3A and 3B show a densitometer according to this invention as a dual optical channel system. It, however, should be understood that this invention may be reduced to practice in the form of mono-optical channel system. Then, in operation, first the cell is filled with a medium for determining a standard value, and thereafter the medium is replaced by a solution to be tested.

Figure 5:
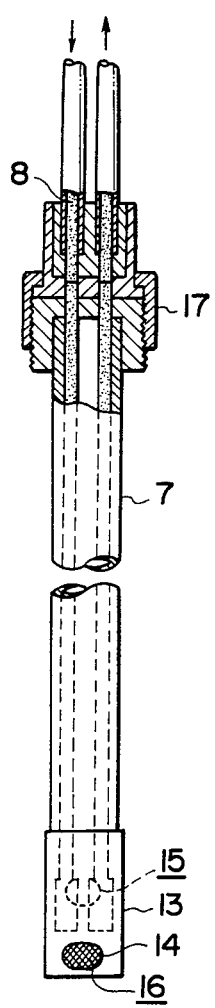
FIGS. 5–7 show the structure of a densitometer according to the invention.
Figure 6:
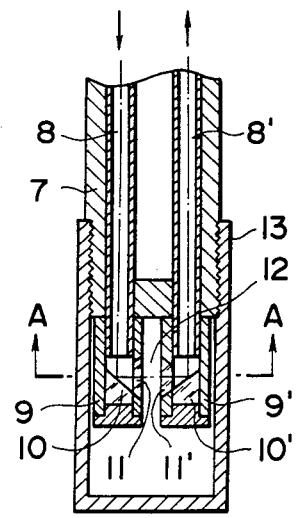
Figure 7:
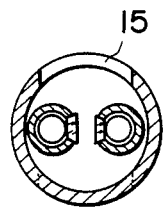

Referring to FIGS. 5-7 there is shown, in detail, the structure of a densitometer according to this invention. Specifically FIG. 5 shows an elevation of the turbidimeter, partly in section, and FIG. 6 is a longitudinal section of a detecting part of the instrument at a somewhat enlarged scale. FIG. 7 shows a cross-section of the detecting part taken along line "A"—"A" and viewed in the direction indicated by arrows. As shown, a pipe 7 is detachably connected to an upper shank with a cap nut 17. A pair of optical fibers 8 and 8' extend in the inner space of the pipe 7. These optical fibers end at the terminal portion of the pipe 7. One of the optical fibers is optically connected to a light source (not shown) whereas the other optical fiber 8' is optically connected to a photodetector (not shown). As shown in detail in FIG. 6, a detachable end cap 13 is threadly engaged with the closed end of the tube to define a cell space. Two opposite hollow extensions 9, 9' are fixed to the closed end of the pipe. The optical fibers 8 and 8' extend, and end in the hollow space of the extensions 9 and 9'. Each extension has a diffuser 11 or 11' at its side facing towards the other counterpart. These extensions, also have mirrors 10 and 10' respectively, and the mirrors are positioned so as to define an optical path along which the light from one optical fiber 8 passes to the other optical fiber 8' via mirror 10, diffuser 11 inter-extension space, diffuser 11' and mirror 10'. As shown in FIG. 5 the end cap has a lower aperture 16 and an upper aperture 15. Preferably, the lower aperture has a fine net thereacross for the reasons described below.

In operation, the instrument is immersed in a bath of suspension, thus filling the cell space with the suspension. Then the light from a light source travels the optical fiber 8 to fall on the mirror 10. The light is reflected by the mirror 10 to pass through the diffuser 11, the interspace in the cell and the diffuser 11' before falling on the mirror 10'. The transmitted light travels the other optical fiber 8' towards a photodetector. As mentioned earlier, the light when passing through the first diffuser 11, is converted to diffused light, and every ray of scattered light as a result of collision against particles in suspension, reaches the second diffuser 11', where it is converted into a diffused light, a component of which is reflected by the mirror 10' to travel toward the photodetector via the optical fiber 8'.

When a suspension flows, the instrument is immersed in the flowing suspension with the meshed inlet of the end cap upstream and the vacant outlet downstream, thereby preventing any bubbles from entering the cell space. A helium neon laser (5 mv, 632.8 nm) or a tungsten lamp (30 w) was used as a light source. A silicon photocell (HAMAMASU TV K.K. 5876) was used as a photodetector. The instrument was used in monitoring the growth of yeast cells in culture broths. The optical density vs. concentration (dry cell mass concentration of yeast cells in a culture broth) characteristics showed substantial linearity over an extensive range. The monitoring result was given in FIG. 8. As is readily understood, the wide range linearity of a turbidimeter according to this invention facilitates the designing of full automation of fermentation.

What is claimed is:

1. An instrument for measuring the concentration of a suspension within a cell in terms of its optical density comprising a tubular housing accommodating a pair of light conducting means, one having a light emitting end for supplying light to the suspension within the cell and the other having a light receiving end for receiving light from the suspension within the cell and supplying it to an optical density measuring means, said light emitting and receiving ends being spaced apart to transmit light to and receive light from a space within the cell for the suspension to be measured, and light diffusing means intermediate said light emitting end and said space for sufficiently diffusing the light emitted to the suspension within said space to provide a substantially linear relationship between the measured optical density and the concentration of the suspension, and a cap at one end of said tubular housing, the interior of said end cap defining the cell, and wherein inlet and outlet apertures are spaced apart in said cap, one closer to the end of the cap and the other more remote from the end, and wherein said inlet aperture is provided with a mesh to prevent bubbles from entering the space within the cell.

2. An instrument as set forth in claim 1 in which the light diffusing means is accommodated within the cell adjacent said space.

3. An instrument as set forth in claim 1 including light diffusing means intermediate said space and said light receiving end for further diffusing the light supplied to the said receiving end of the light conducting means.

4. An instrument as set forth in claim 3 including parallel extensions within the cell for said light conducting means, one extension communicating with the light emitting end and the other communicating with the light receiving end, each extension accommodating one of the light diffusing means, the light diffusing means being arranged in opposing relationship to define between them said space for the suspension to be measured.

5. An instrument as set forth in claim 4 including a mirror accommodated within each of the extensions intermediate the respective end of the light conducting means and the diffusing means, one mirror deflecting the light from said emitting end through the diffusing means to the space and the other mirror deflecting the light from the space through the diffusing means to the said receiving end.

* * * * *